United States Patent
Krasnov et al.

(10) Patent No.: US 10,753,883 B2
(45) Date of Patent: Aug. 25, 2020

(54) METHOD AND SYSTEM FOR DETECTING INCLUSIONS IN FLOAT GLASS

(71) Applicant: GUARDIAN GLASS, LLC, Auburn Hills, MI (US)

(72) Inventors: Alexey Krasnov, Canton, MI (US); Xuequn Hu, Northville, MI (US); Robert Broadwater, Ann Arbor, MI (US); Greg Gaudet, Ann Arbor, MI (US)

( * ) Notice: Subject to any disclaimer, the term of this patent is extended or adjusted under 35 U.S.C. 154(b) by 191 days.

(21) Appl. No.: 15/615,903

(22) Filed: Jun. 7, 2017

(65) Prior Publication Data

US 2018/0356346 A1   Dec. 13, 2018

(51) Int. Cl.

| | |
|---|---|
| *G01K 3/00* | (2006.01) |
| *G01K 17/00* | (2006.01) |
| *G01J 5/00* | (2006.01) |
| *G01N 21/896* | (2006.01) |
| *G01N 21/958* | (2006.01) |
| *G01N 33/38* | (2006.01) |

(Continued)

(52) U.S. Cl.
CPC ........... *G01N 21/896* (2013.01); *C03B 18/02* (2013.01); *C03C 3/087* (2013.01); *G01J 5/0022* (2013.01); *G01J 5/0066* (2013.01); *G01J 5/0896* (2013.01); *G01N 21/552* (2013.01); *G01N 21/88* (2013.01); *G01N 21/8903* (2013.01); *G01N 21/958* (2013.01); *G01N 25/72* (2013.01); *G01N 33/386* (2013.01); *G01J 2005/0029* (2013.01); *G01J 2005/0077* (2013.01)

(58) Field of Classification Search
USPC .................................. 374/121, 4, 5, 57, 124
See application file for complete search history.

(56) References Cited

U.S. PATENT DOCUMENTS

| | | | |
|---|---|---|---|
| 3,083,551 | A | 4/1963 | Pilkington |
| 3,220,816 | A | 11/1965 | Pilkington |
| | | (Continued) | |

FOREIGN PATENT DOCUMENTS

| | | |
|---|---|---|
| CN | 104597081 | 5/2015 |
| DE | 10 2013 002 602 A1 | 8/2014 |

OTHER PUBLICATIONS

U.S. Appl. No. 16/148,057, filed Oct. 1, 2018; Agbuga.
(Continued)

*Primary Examiner* — Mirellys Jagan

(57) ABSTRACT

A method and/or system is provided for detecting inclusions (e.g., nickel sulfide based inclusions/defects) in soda-lime-silica based glass, such as float glass. In certain example instances, during and/or after the glass-making process, following the stage in the float process where the glass sheet is formed and floated on a molten material (e.g., tin bath) and cooled or allowed to cool such as via an annealing lehr, visible light from an intense visible light source(s) is directed at the resulting glass and thermal imaging is used to detect inclusions based on a temperature difference between the inclusions and surrounding float glass. In another example embodiment, inclusion detection may be performed without exposure of the glass to light from a light source(s). Inclusions and surrounding glass may cool at different rates and be at different temperatures just prior to and/or after an annealing lehr, and a difference in residual temperature between inclusions and surrounding glass may be detected via thermal imaging and identified to identify inclusion(s).

30 Claims, 3 Drawing Sheets

(51) Int. Cl.

| | |
|---|---|
| *G01N 21/552* | (2014.01) |
| *G01N 21/88* | (2006.01) |
| *G01N 21/89* | (2006.01) |
| *C03C 3/087* | (2006.01) |
| *G01N 25/72* | (2006.01) |
| *G01J 5/08* | (2006.01) |
| *C03B 18/02* | (2006.01) |

(56) References Cited

U.S. PATENT DOCUMENTS

| | | |
|---|---|---|
| 3,814,946 A | 6/1974 | Takahashi et al. |
| 3,954,432 A | 5/1976 | Hummel et al. |
| 5,214,008 A | 5/1993 | Beckwith et al. |
| 6,388,745 B2 | 5/2002 | Stevens et al. |
| 6,403,509 B2 | 6/2002 | Cochran et al. |
| 6,610,622 B1 | 8/2003 | Landa et al. |
| 6,953,759 B2 | 10/2005 | Landa et al. |
| 7,169,722 B2 | 1/2007 | Landa et al. |
| 7,511,807 B2 | 3/2009 | Fang et al. |
| 7,743,630 B2 | 6/2010 | Krasnov et al. |
| 8,677,782 B2 | 3/2014 | Disteldorf et al. |
| 9,016,094 B2 | 4/2015 | Siess et al. |
| 10,481,097 B1 | 11/2019 | Agbuga |
| 2014/0157827 A1 | 6/2014 | Simpson |
| 2016/0102010 A1 | 4/2016 | Beall et al. |

OTHER PUBLICATIONS

U.S. Appl. No. 16/295,099, filed Mar. 7, 2019; Krasnov et al.
U.S. Appl. No. 16/295,141, filed Mar. 7, 2019; Krasnov et al.
Schittich et al., "Glass Construction Manual" $2^{nd}$ Revised and Expanded Edition 2007, Munich, Germany.
Musgraves et al., "Springer Handbook of Glass" published by Springer Nature Switzerland AG.

Fig. 1  Absorption spectrum of NiS inclusions

Fig. 2  Transmission spectrum of regular float glass.

METHOD AND SYSTEM FOR DETECTING INCLUSIONS IN FLOAT GLASS

Example embodiments of this invention relates to a method and/or system for detecting inclusions (e.g., nickel sulfide based inclusions/defects) in soda-lime-silica based glass, such as float glass. In certain example embodiments of this invention, visible light from an intense visible light source(s) is directed at the glass, and thermal imaging is used to detect inclusions based on a temperature difference between the inclusions and surrounding glass. In an example embodiment of this invention, during and/or after the glass-making process, following the stage in the float process where the glass sheet is formed and floated on a molten material (e.g., tin bath) and cooled or allowed to at least partially cool such as after an annealing lehr, at least visible light from a light source(s) is directed at the resulting glass and thermal imaging is used to detect inclusions based on a temperature difference between the inclusions and surrounding float glass. In another example embodiment of this invention, the inclusion detection may be performed without exposure of the glass to light from a light source(s). Inclusions and surrounding glass cool at different rates and are at different temperatures just prior to and/or after the annealing lehr, and a difference in residual temperature between inclusions and surrounding glass may be detected via thermal imaging and identified to identify an inclusion.

BACKGROUND OF THE INVENTION

The process of making float glass is known in the art. For example, see U.S. Pat. Nos. 3,954,432, 3,083,551, 3,220,816, 7,743,630, 8,677,782, 9,016,094, and 5,214,008, the disclosures of all of which are hereby incorporated herein by reference. Generally speaking, in a float glass-making line, batch materials are heated in a furnace or melter to form a glass melt. The glass melt is poured onto a bath of molten material such as tin (tin bath) and is then continuously cooled to form a float glass ribbon. The float glass ribbon is then forwarded to an annealing lehr for further processing and then may be cut to form solid glass articles, such as flat glass sheets. For float glass, the glass batch often includes soda, lime and silica to form soda-lime-silica based flat glass.

Float glass is widely used for windows in commercial and residential buildings, glass furniture, shower doors, and automotive windshields. For many products, float glass must be thermally tempered (undergo heating to at least 580 degrees C., followed by a rapid cooling) to ensure safety in case of breakage. Impurities from raw materials, sulfur from additive(s), and/or contaminations from the float process occasionally and unpredictably form unwanted chemical compounds (e.g., inclusions) during glass formation, which are undesirable defects in the glass. Nickel, for example, is known to spontaneously bond with sulfur to form inclusions of or based on nickel sulfide (of any suitable stoichiometry such as NiS).

Although typically harmless in annealed glass (e.g., made via the float process without any additional heat treatment such as thermal tempering), NiS inclusions are known for causing spontaneous breakage of thermally tempered glass. Moreover, NiS inclusions/defects in thermally tempered glass have caused catastrophic glass failure over long periods of time in installed products. Rejecting defective annealed glass, therefore, serves at least two purposes: a) increase production yield during the expensive thermal tempering and heat soaking stages, and b) minimize catastrophic failures of glass in installed products.

Nickel sulfide exists in different phases at different temperatures. For instance, two specific phases of NiS known are the alpha-phase and the beta-phase. At temperatures below 715 degrees F. (379 C), nickel sulfide is relatively stable in the beta-phase form. Above this temperature, it is stable in the alpha-phase. Therefore, when glass is produced in a furnace, it is likely that any NiS inclusions will be in the alpha-phase. In typical annealed glass, the slow cooling process provided by the annealing lehr allows the NiS ample time to transform to its beta-phase as the glass cools. However, in the fast cooling process used in both heat-strengthened and tempered glass, there is often insufficient time to complete the phase transition (which is a relatively slow process). The NiS inclusions are therefore trapped in the glass in their high-temperature alpha-phase. However, once the glass cools past the phase change temperature, the NiS inclusion seeks to reenter the lower energy beta-phase. For trapped inclusions, this process takes anywhere from months to years. This may have no effect on glass, were it not for the point that when the NiS changes from alpha-phase to beta-phase, it increases in volume such as by 2-4%. This expansion may create localized tensile stresses which can lead to glass failures.

Nickel sulfide is a compound that comes in various forms as well. The most common forms of nickel sulfide are $Ni_7S_6$, NiS, $NiS_{1.03}$, $Ni_3S_2$ and $Ni_3S_2+Ni$. When viewed under an electron microscope, $Ni_7S_6$, NiS, and $NiS_{1.03}$ are yellow-gold in color and have a rugged surface similar to a golf ball. These three types are non-magnetic and have been found to cause failure in tempered glass.

Various methods have been used for inline detection of NiS inclusions and other micro-defects of similar size scale (e.g., 50-150 microns sized defects). U.S. Pat. No. 7,511,807, incorporated herein by reference, for example directs light at the glass and looks for light scattering in order to detect inclusions. The detection cross-section in such a manner, however, is small around the same as the defect size. Conventional techniques for detecting inclusions therefore have been inefficient and sometimes ineffective.

In view of the above, it will be apparent that there exists a need in the art for an improved method of making glass, and controlling glass quality, including an improved method and/or apparatus for detecting inclusions in soda-lime-silica based glass.

SUMMARY OF EXAMPLE EMBODIMENTS OF THE INVENTION

A method and/or system is provided for detecting inclusions (e.g., nickel sulfide based inclusions/defects) in soda-lime-silica based glass. In certain example embodiments, the soda-lime-silica based glass comprises a base glass portion that includes, by weight percentage: $SiO_2$ 67-75%, $Na_2O$ 10-20%, CaO 5-15%, $Al_2O_3$ 0-7%, MgO 0-7%, and $K_2O$ 0-7%. Optionally, a colorant portion of the glass may further include one or more colorants such as iron, selenium, cobalt, erbium and/or the like.

In certain example embodiments of this invention, during the glass-making process, following the stage in the float process where the glass sheet is formed and floated on a molten material (e.g., tin bath), and at least partially cooled or allowed to at least partially cool such as at or after an annealing lehr, visible light from an intense visible light source(s) (e.g., flash lamp(s), laser(s), or the like) is directed at the glass and thermal imaging of the glass is used to detect inclusions based on a temperature difference between the inclusions and surrounding float glass. The light source may be pulsed or continuous in different example embodiments. The inclusions are thus detected based on temperature difference, or relatively high temperature spots/areas. It has been found that the temperature difference is present because the inclusions (e.g., nickel sulfide based inclusions, or other types of metal based inclusions) have been determined to be more absorbing of the wavelengths used (visible and/or near-IR) than is the surrounding float glass, and thus heat up more and retain thermal energy longer than the surrounding glass when exposed to an intense dose of such wavelengths. Such an inclusion detection process may also be utilized during or after manufacture of other types of glass such as borosilicate glass, aluminosilicate glass, or the like (as opposed to during or after a float process for making soda-lime-silica based glass), and may be located after an annealing lehr of a float process or any other suitable process in certain example embodiments. The temperature difference based inclusion detection process, located at or after the annealing lehr, and before and/or after a glass cutting station, in either a float or other glass making process, is advantageous in that it allows inclusions in soda-lime-silica based glass to be detected more easily and more efficiently, and thus glass failures during implementation in buildings and so forth to be reduced. Glass made in this manner, after passing the detection station with no inclusions being detected, is useful, for example and without limitation, in glass window applications for buildings and/or vehicles, solar cell applications, furniture glass applications, and/or display glass applications.

In certain example embodiments of this invention, there is provided a method of detecting an inclusion in glass, the glass including a base glass composition comprising: $SiO_2$ 67-75%, $Na_2O$ 10-20%, CaO 5-15%, $Al_2O_3$ 0-7%, $K_2O$ 0-7%, the method comprising: directing light from at least one light source toward the glass, the light comprising a wavelength(s) for selectively heating inclusions to an extent more than the glass; and thermal imaging for detecting an inclusion in the glass based at least on a temperature difference between the inclusion (e.g., nickel sulfide inclusion, or other type of metal based inclusion) and another area of the glass.

In another example embodiment of this invention, the inclusion detection may be performed without exposure of the glass to light from a light source(s). Inclusions and surrounding glass cool at different rates and are at different temperatures just prior to and/or after the annealing lehr, and a difference in residual temperature between inclusions and surrounding glass may be detected via thermal imaging and identified to identify an inclusion.

DETAILED DESCRIPTION OF CERTAIN EXAMPLE EMBODIMENTS OF THIS INVENTION

Figure 1:
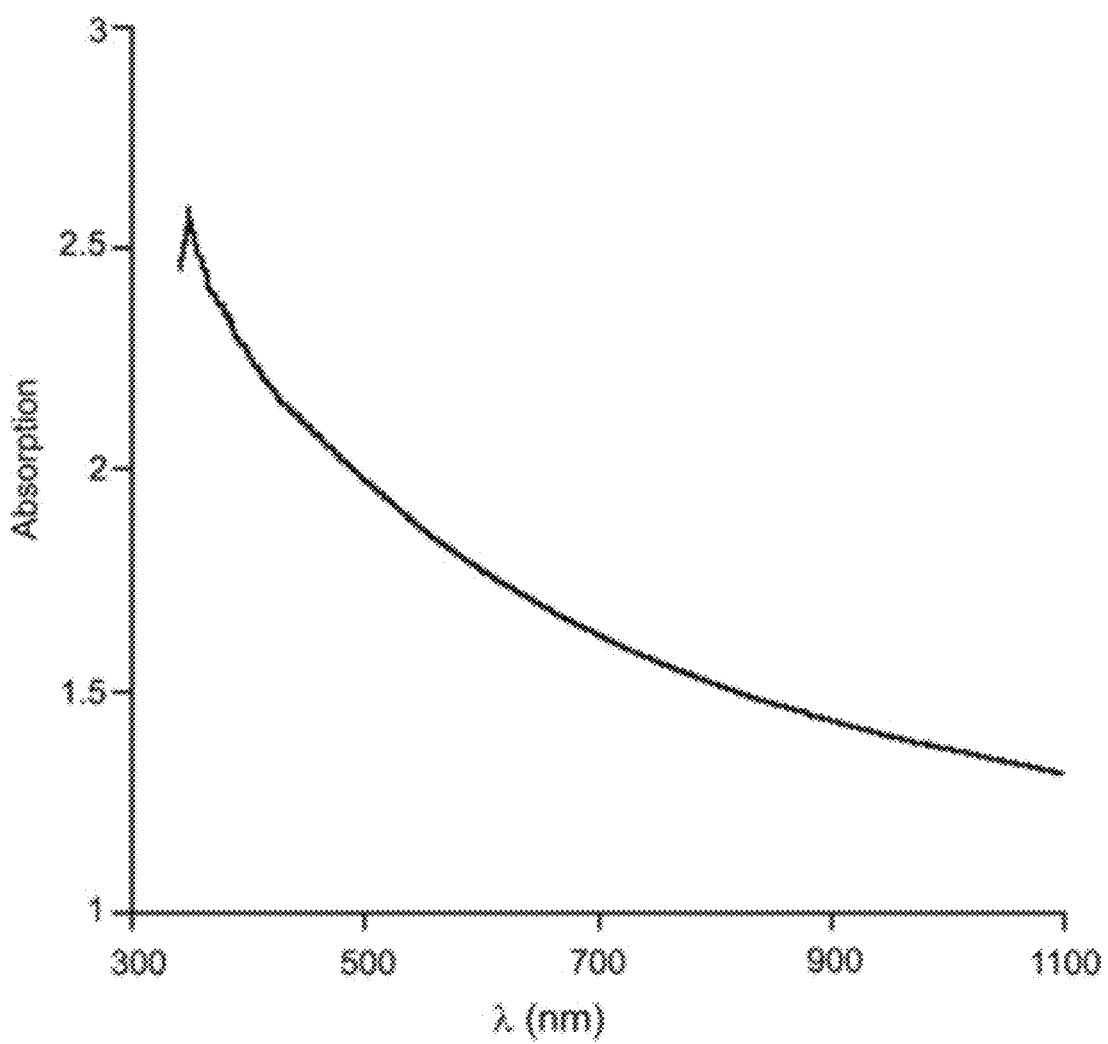
FIG. 1 is a graph illustrating the absorption of nickel sulfide inclusions that may be present in float glass, versus wavelength (nm).

A method and/or system is provided for detecting inclusions (e.g., nickel sulfide based inclusions/defects) in soda-lime-silica based glass 1. In certain example embodiments, the soda-lime-silica based glass 1 comprises a base glass portion that includes, by weight percentage: $SiO_2$ 67-75%, $Na_2O$ 10-20%, CaO 5-15%, $Al_2O_3$ 0-7%, MgO 0-7%, and $K_2O$ 0-7%. Optionally, a colorant portion of the glass may further include one or more colorants such as iron, selenium, cobalt, erbium and/or the like. Alternatively, the glass 1 may be a different type of glass such as borosilicate glass, aluminosilicate glass, or the like.

An example soda-lime-silica base glass 1 according to certain embodiments of this invention that may be made via the float process or other suitable process, on a weight percentage basis, includes the following basic ingredients:

TABLE 1

| Example Base Glass | |
|---|---|
| Ingredient | Wt. % |
| $SiO_2$ | 67-75% |
| $Na_2O$ | 10-20% |
| CaO | 5-15% |
| MgO | 0-7% |
| $Al_2O_3$ | 0-7% |
| $K_2O$ | 0-7% |

Other minor ingredients, including various refining aids, such as salt cake, crystalline water and/or the like may also be included in the base glass. In certain embodiments, for example, glass 1 herein may be made from batch raw materials silica sand, soda ash, dolomite, limestone, with the use of salt cake ($SO_3$) as a refining agent. Reducing and oxidizing agent(s) may also be used in certain instances. In certain instances, soda-lime-silica base glasses 1 herein may include by weight from about 10-15% $Na_2O$ and from about 6-12% CaO. In addition to the base glass materials discussed above, the glass batch and/or final glass 1 may also include a colorant portion including material(s) such as iron, erbium, cobalt, selenium and/or the like in suitable amounts in order to provide coloration and/or absorption to the glass in a desired manner. In certain example embodiments of this invention, the amount of total iron in the glass may be from about 0.05 to 1.2%, more preferably from about 0.3 to 0.8%. In the case of certain clear high transmission glasses, the total iron may be from about 0.005 to 0.025%. The total amount of iron present in the glass, and thus in the colorant portion thereof, is expressed herein in terms of $Fe_2O_3$ in accordance with standard practice. This, however, does not imply that all iron is actually in the form of $Fe_2O_3$. Likewise, the amount of iron in the ferrous state is reported herein as FeO, even though all ferrous state iron in the glass may not be in the form of FeO.

When making the glass via the float process for example, the glass batch raw materials (e.g., silica sand, soda ash, dolomite, limestone, colorant(s), etc.) are provided in and heated in a furnace or melter to form a glass melt. The glass melt is poured onto a bath of molten material such as tin (tin bath), where the glass is formed and continuously cooled to form a float glass ribbon. The float glass ribbon proceeds toward an annealing lehr for slow cooling. Optionally, prior to entering the annealing lehr, lateral edge portion(s) of the glass sheet may be trimmed in a hot condition. The glass sheet typically reaches the beginning of the annealing lehr at a temperature of at least about 540 degrees C., more preferably at least about 580 degrees, C, with a possible range from about 540 (or 580) to 800 degrees C. During the annealing, the temperature of the glass sheet strip is slowly cooled from the annealing point (e.g., from about 538-560 degrees C.) to a strain point of from about 495-560 degrees C., which may be referred to as an annealing range. While these temperature ranges are preferred for annealing, different temperatures may be used in certain instances. The continuous glass sheet may be supported by either rollers or gas during annealing. After annealing, the continuous glass sheet is moved on for further processing such as one or more of cutting, additional cooling, coating and/or the like.

Figure 3:
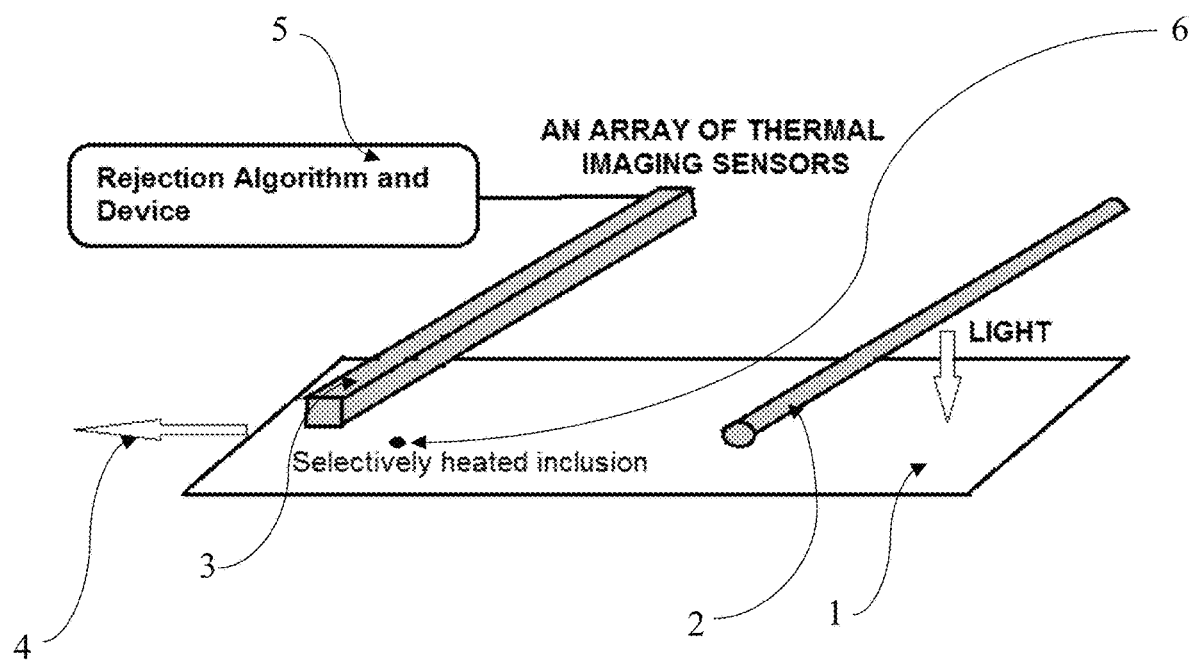
FIG. 3 is a schematic diagram of a system for detecting inclusions in float glass according to an example embodiment of this invention.

The system shown in FIG. 3 for detecting inclusions 6, such as nickel sulfide (of any stoichiometry) based inclusions or other metal based type of inclusions, in the glass 1 may be located on the float line after the annealing lehr, and before or after a glass cutting station, in certain example embodiments of this invention. When inclusion(s) 6 are found in the glass, that portion of the glass is discarded and/or not subjected to thermal tempering. Alternatively, the inclusion detecting system shown in FIG. 3 may instead be located separate from the float line, such as at a station between the float line and a tempering furnace, or at a station just prior to a tempering furnace in a tempering facility, in order to detect inclusions 6 and discard glass with inclusions prior to thermal tempering. Such an inclusion detection process may also be utilized during or after manufacture of other types of glass such as borosilicate glass, aluminosilicate glass, or the like (as opposed to during or after a float process for making soda-lime-silica based glass)

In certain example embodiments of this invention, referring to FIG. 3 for instance, during the glass-making process such as the float process, following the stage in the float process where the glass sheet is formed and floated on a molten material (e.g., tin bath) and cooled or allowed to at least partially cool such as after an annealing lehr, visible light from an intense visible light source(s) (e.g., flash lamp(s), laser(s), or the like) 2 is directed at the glass 1 and thermal imaging of the glass via at least a thermal imaging detector/sensor 3 is used to detect inclusions (e.g., nickel sulfide inclusions) 6 based on a temperature difference between the inclusions 6 and surrounding float glass 1. The light source(s) 2 may be pulsed or continuous in different example embodiments, and may be a single source or an array of light sources. The inclusions 6 in the glass 1 are thus detected based on temperature difference, or relatively high temperature spots/areas, via thermal imaging.

It has been found that the temperature difference between the inclusions 6 and the surrounding soda-lime-silica based glass 1 is present because the NiS inclusions have been determined to be more absorbing of the wavelengths used than is the surrounding float glass, and thus heat up more than the surrounding glass when exposed to an intense dose of such wavelengths. The temperature difference based inclusion detection process, located at or after the annealing lehr, and before and/or after a glass cutting station, in either a float or other glass making process, is advantageous in that it allows inclusions in soda-lime-silica based glass to be detected more easily and more efficiently, and thus glass failures during implementation in buildings and so forth to be reduced. Glass made in this manner, after passing the detection station with no inclusions being detected, is useful, for example and without limitation, in glass window applications for buildings and/or vehicles, solar cell applications, furniture glass applications, and/or display glass applications.

Thus, example embodiments of this invention relate to an improved method and/or system for detecting inclusions 6, such as NiS based inclusions, and other defects in glass 1 such as soda-lime-silica based glass which may be made via the float process. It has been found that there are wavelengths to which glass 1 is generally transparent, but NiS inclusions are not. These wavelengths mostly are in the visible region of the spectrum. Moreover, it has been found that the detection cross-section of thermal imaging is greater than that of visible imaging. It has been found that the immediate area of glass around an NiS or another opaque inclusion 6 will have an elevated temperature if the inclusion 6 is selectively heated.

Figure 2:
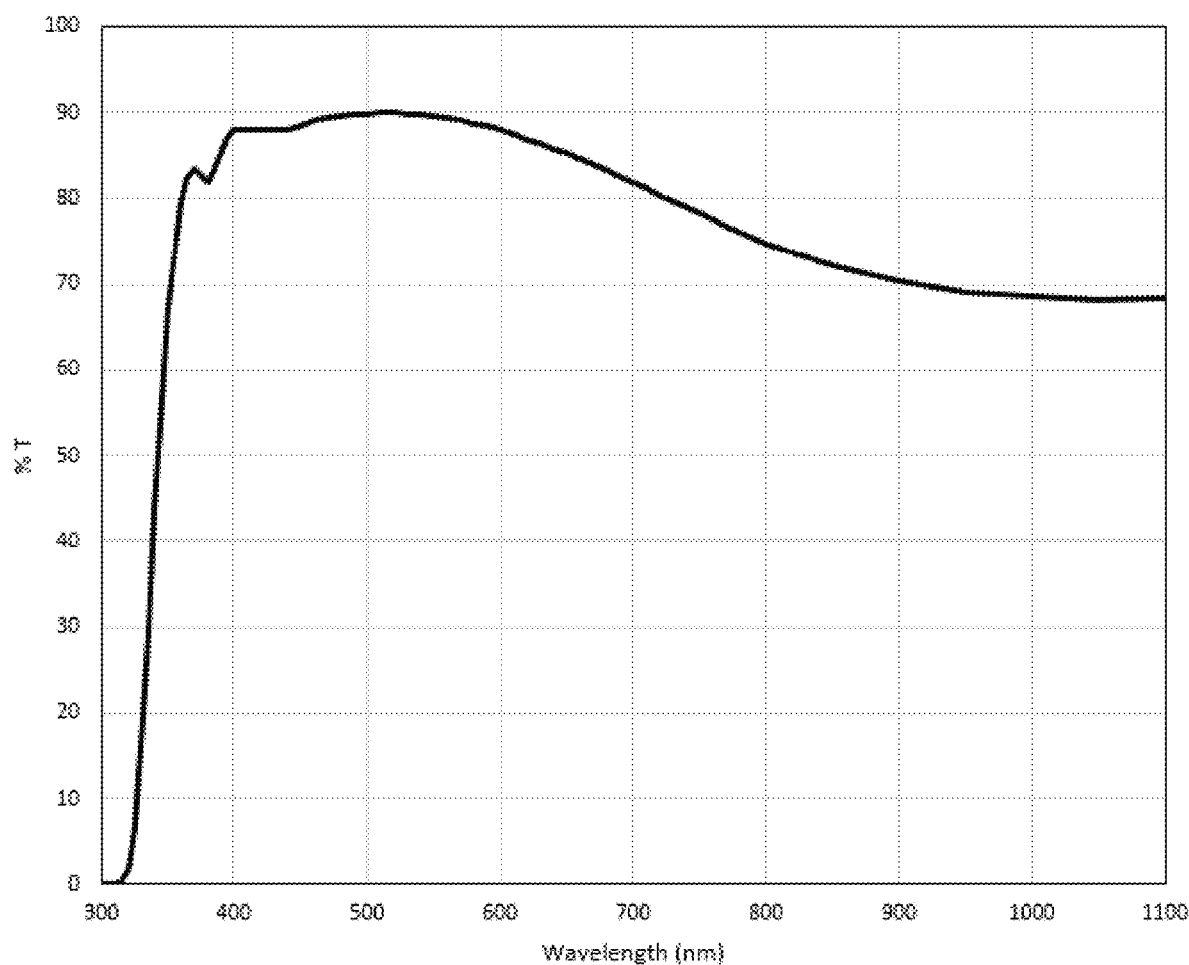
FIG. 2 is a graph illustrating the transmission (% T) of an example soda-lime-silica based float glass, versus wavelength (nm).

As shown in FIGS. 1-2, NiS is generally an opaque material, which makes it absorbent to certain light wavelengths for which glass is transparent. Float glass 1, for instance, is substantially absorbent in ultra-violet (UV) and near-infrared (NIR) regions. At the same time, visible wavelengths (400-700 nm) and even some near IR pass through glass 1 with ease as shown in FIG. 2.

FIG. 3 illustrates an example system and method of detecting inclusions 6 in glass according to an example embodiment of this invention. In the FIG. 3 embodiment, the glass 1 moves in direction 4 and passes under light source(s) 2 and then thermal sensor(s) 3. Intense visible light from source(s) 2 heats the opaque micro-inclusions 6 without significantly heating the glass 1, due to the difference in absorption between the inclusions and the surround glass shown in FIGS. 1-2. The elevated thermal signature of these inclusions 6 is detected via thermal imaging sensor(s) 3 and analyzed with the help of thermal imaging software and/or firmware in the form of an algorithm stored in a processor 5 including processing circuitry, for detecting the presence of inclusions 6. The detection cross-section of the thermal imaging technique is greater than that of the detection systems working in the visible spectral region. The explanation of this effect comes from the diffraction nature of light waves. The long waves (IR), on which thermal imaging is based, diffract on larger defects and thus their image is smeared more than that of the visible waves, resulting in a larger detection cross-section compared to the visible region. For example, if the processor 5 detects a temperature difference of at least 1 degree F. (more preferably at least 2 degrees F., and possibly at least 3 degrees F.) between a given area (e.g., 6) and the surrounding glass 1, it is determined that an inclusion is, or may be, present in the area 6 with the higher temperature. The processor 5 may utilize an area-mapping or line-scanning thermal imaging system, an X-Y defect positioning algorithm and device, and optionally an additional device and algorithm capable of identifying the nature of the defect, in certain example embodiments of this invention.

The heating visible light source 2 may be a flash-light lamp or a set of lamps, or a laser operating in the visible range of the optical spectrum. The light source 2 can operate at a single wavelength or combine several wavelengths at which the glass 1 is transparent and micro-inclusions 6 are not. In the FIG. 3 example embodiment, glass 1 passes under source(s) 2 of intense light of specific wavelength(s) (e.g., including in a range from 350 and 1500 nm, more preferably from 400-1100 nm, more preferably from 400-1000 nm, and most preferably in a range from 400 to 700 nm), such as an intense flash lamp(s). Visible light from the source(s) 2 is significantly absorbed only by substantially optically-absorbing NiS and/or other opaque inclusions 6, but not significantly by the glass 1. This selective light absorption creates a temperature difference between the inclusions 6 and the surrounding glass 1 as discussed above, which can be sensed by thermal sensor(s) 3 that may operate in at least part of the IR spectrum. The glass areas immediately surrounding the inclusions 6 also gain additional temperature due to heat transfer, thus expanding the heated area and the effective detection cross-section area for the processor 5. Thermal imaging is then used by the processor 5, including processing circuitry which receives data from the thermal sensor(s) 3, to detect the inclusions and other micro-defects 6 as spots with elevated temperature compared to temperature of the bulk of the glass 1. Since thermal imaging operates in a long-wavelength range, its effective imaging cross-section is greater than that of the techniques using the visible light. Upon detecting the inclusions 6, the defective glass undergoes a pass/reject algorithm, i.e., it is either rejected or sent for a detailed identification of inclusions. If no inclusions (e.g., NiS based inclusions) are detected, the glass may still be used in production.

In other example embodiments, a flash lamp(s) 2 and the thermal imaging sensor(s) 3 may be passed over a stationary glass sheet 1 for inclusion detection.

In an example embodiment, the thermal imaging sensor(s) 3 may be a one-dimensional array (e.g., linear array) or two dimensional array, of IR sensors positioned in a proximity to the glass 1. For example, the IR sensor(s) may detect thermal differences and/or thermal measurements in any wavelength(s) ranges in a range of from about 900 nm to 8000 nm, more preferably from about 1000-3000 nm. In certain example embodiments, a laser operating in the visible (such as a standard 532 nm diode-pumped solid-state laser) may be used as the light source(s) 2 for heating the defects 6. The light source(s) 2 may be a laser or a set of lasers, optionally with an optically-defocusing member.

In another example embodiment, the inclusion 6 detection may be performed without exposure of the glass to light from a source(s) 2. Instead, it may be done inline during glass production when the float glass is cooled down to a temperature at which there is a temperature gradient between the inclusions 6 and the glass 1, such as prior to and/or soon after the annealing lehr in the float process. Inclusions 6 and the surrounding glass cool at different rates and are at different temperatures just prior to and/or after the annealing lehr, and different in residual temperature between inclusions and surrounding glass may be detected and identified to identify an inclusion. In this example embodiment, the identification of different defects may be done based on the difference of their cooling rates due to the difference in their specific gravity (the intense light source 2 is not needed). One or a plurality of thermal detectors may be used to measure temperature data from the hot or warm glass, so that temperature data may be analyzed to identify temperature differences between inclusion areas and surrounding glass areas based on different in thermal capacitance, in order to identify inclusions in the glass, as explained herein.

In an example embodiment of this invention, there is provided a method of detecting an inclusion in glass, the glass may include a base glass composition comprising: $SiO_2$ 67-75%, $Na_2O$ 10-20%, CaO 5-15%, $Al_2O_3$ 0-7%, $K_2O$ 0-7% (or the glass may be another type of glass such as borosilicate glass, aluminosilicate glass, or the like), the method comprising: directing light from at least one light source toward the glass, the light comprising a wavelength(s) for selectively heating inclusions to an extent more than the glass; and thermal imaging for detecting an inclusion in the glass based at least on a temperature difference between the inclusion and another area of the glass.

In the method of the immediately preceding paragraph, the at least one light source may direct light having a wavelength(s) in a range from 400-1100 nm, more preferably from 400 to 700 nm, toward the glass.

In the method of any of the preceding two paragraphs, the inclusion may comprise nickel sulfide.

In the method of any of the preceding three paragraphs, the glass may further comprises a colorant portion comprising iron.

In the method of any of the preceding four paragraphs, said detecting the inclusion may comprise determining whether an area of the glass is at a temperature higher than a temperature of said another area of the glass by at least a predetermined amount, and when the area of the glass is at a temperature higher than a temperature of said another area of the glass by at least the predetermined amount determining that the area of the glass may have an inclusion. The predetermined amount may be 1 degree F., more preferably 2 degrees F., and possibly 3 degrees F. In certain example embodiments, the predetermined amount may be at least 1 degree F., more preferably at least 2 degrees F., and possibly at least 3 degrees F. (e.g., 3, 4, or 5 degrees F.).

The method of any of the preceding five paragraphs may further comprise moving the glass under the at least one light source and/or under at least one thermal imaging sensor.

In the method of any of the preceding six paragraphs, said at least one light source may comprises a flash lamp and/or a laser.

The method of any of the preceding seven paragraphs may further comprise determining whether to pass or reject the glass based at least on whether an inclusion is detected.

In the method of any of the preceding eight paragraphs, the thermal imaging for detecting an inclusion in the glass based at least on a temperature difference may comprise at least one IR sensor sensing temperature data based at least on at least one wavelength in a range of from 900 nm to 8000 nm (more preferably from 1000 nm to 3000 nm), and analyzing said data in order to detect the temperature difference.

In the method of any of the preceding nine paragraphs, the light source may be located on and/or in a float line, and may be positioned after an annealing lehr of the float line.

Once given the above disclosure many other features, modifications and improvements will become apparent to the skilled artisan. Such features, modifications and improvements are therefore considered to be a part of this invention, the scope of which is to be determined by the following claims:

What is claimed is:

1. A method of detecting an inclusion in glass, the glass including a base glass composition comprising:

| Ingredient | wt. % |
|---|---|
| $SiO_2$ | 67-75% |
| $Na_2O$ | 10-20% |
| CaO | 5-15% |
| $Al_2O_3$ | 0-7% |
| $K_2O$ | 0-7% | the method comprising:
 directing light from at least one light source toward the glass, the light comprising a wavelength(s) for selectively heating inclusions to an extent more than the glass; and
 thermal imaging for detecting an inclusion in the glass based at least on a temperature difference between the inclusion and another area of the glass.

2. The method of claim 1, wherein the at least one light source directs light having a wavelength(s) in a range from 400 to 700 nm toward the glass.

3. The method of claim 1, wherein the inclusion comprises nickel sulfide.

4. The method of claim 1, wherein the glass further comprises a colorant portion comprising iron.

5. The method of claim 1, further comprising moving the glass under the at least one light source and/or under at least one thermal imaging sensor.

6. The method of claim 1, wherein said at least one light source comprises a flash lamp.

7. The method of claim 1, wherein said at least one light source comprises a laser.

8. The method of claim 1, further comprising determining whether to pass or reject the glass based at least on whether an inclusion is detected.

9. The method of claim 1, wherein said thermal imaging for detecting an inclusion in the glass based at least on a temperature difference comprises at least one IR sensor sensing temperature data based at least on at least one wavelength in a range of from 900 nm to 8000 nm, and analyzing said data in order to detect the temperature difference.

10. The method of claim 1, wherein said thermal imaging for detecting an inclusion in the glass based at least on a temperature difference comprises at least one IR sensor sensing temperature data based at least on at least one wavelength in a range of from 1000 nm to 3000 nm, and analyzing said data in order to detect the temperature difference.

11. The method of claim 1, wherein the at least one light source directs light having a wavelength(s) in a range from 400-1100 nm toward the glass.

12. The method of claim 1, wherein the light source is located on and/or in a float line, and is positioned after an annealing lehr of the float line.

13. The method of claim 1, wherein said detecting the inclusion comprises determining whether an area of the glass is at a temperature higher than a temperature of said another area of the glass by at least a predetermined amount, and when the area of the glass is at a temperature higher than a temperature of said another area of the glass by at least the predetermined amount determining that the area of the glass may have an inclusion.

14. The method of claim 13, wherein the predetermined amount is at least 1 degree F.

15. The method of claim 13, wherein the predetermined amount is at least 2 degrees F.

16. The method of claim 13, wherein the predetermined amount is at least 3 degrees F.

17. A method of detecting an inclusion in glass, the method comprising:
  thermal imaging for detecting an inclusion in the glass based at least on a temperature difference between the inclusion and another area of the glass;
  wherein said detecting the inclusion comprises determining whether an area of the glass is at a temperature higher than a temperature of said another area of the glass by at least a predetermined amount, and when the area of the glass is at a temperature higher than a temperature of said another area of the glass by at least the predetermined amount determining that the area of the glass may have an inclusion; and
  determining whether to pass or reject the glass based at least on whether an inclusion is detected.

18. The method of claim 17, wherein the inclusion comprises nickel sulfide.

19. The method of claim 17, wherein the glass comprises a base glass composition comprising:

| Ingredient | wt. % |
| --- | --- |
| $SiO_2$ | 67-75% |
| $Na_2O$ | 10-20% |
| CaO | 5-15% |
| $Al_2O_3$ | 0-7% |
| $K_2O$ | 0-7% | and further comprises a colorant portion comprising iron.

20. The method of claim 17, further comprising directing light from at least one light source toward the glass, the light comprising a wavelength(s) for selectively heating inclusions to an extent more than the glass.

21. The method of claim 17, wherein a difference in residual temperature between inclusions and surrounding glass is detected via thermal imaging and identified to identify inclusion(s), and no light source after an annealing lehr is needed to heat up inclusions and/or the glass for detection of inclusions.

22. A method of making float glass including a base glass composition comprising:

| Ingredient | wt. % |
| --- | --- |
| $SiO_2$ | 67-75% |
| $Na_2O$ | 10-20% |
| CaO | 5-15% |
| $Al_2O_3$ | 0-7% |
| $K_2O$ | 0-7% | the method comprising:
  melting a glass batch and floating a glass ribbon on a bath comprising tin in forming the glass;
  thermal imaging for detecting an inclusion in the glass based at least on a temperature difference between the inclusion and another area of the glass; and
  determining whether to pass or reject the glass based at least on whether an inclusion is detected.

23. The method of claim 22, wherein said detecting the inclusion comprises determining whether an area of the glass is at a temperature higher than a temperature of said another area of the glass by at least a predetermined amount, and when the area of the glass is at a temperature higher than a temperature of said another area of the glass by at least the predetermined amount determining that the area of the glass may have an inclusion.

24. The method of claim 22, further comprising directing light from at least one light source toward the glass, the light comprising a wavelength(s) for selectively heating inclusions to an extent more than the glass.

25. A system for detecting inclusions in glass including a base glass composition comprising:

| Ingredient | wt. % |
| --- | --- |
| $SiO_2$ | 67-75% |
| $Na_2O$ | 10-20% |
| CaO | 5-15% |
| $Al_2O_3$ | 0-7% |
| $K_2O$ | 0-7% | the system comprising:
  at least one light source configured to direct light toward the glass, the light comprising a wavelength(s) for selectively heating inclusions to an extent more than the glass;

at least one thermal sensor configured to sense temperatures of the glass; and a processor, including processing circuitry, configured to receive temperature data from the at least one thermal sensor and detect an inclusion in the glass based at least on a temperature difference between the inclusion and another area of the glass.

26. The system of claim 25, wherein the at least one light source is configured to direct light having a wavelength(s) in a range from 400 to 700 nm toward the glass.

27. The system of claim 25, wherein the inclusion comprises nickel sulfide.

28. The system of claim 25, wherein the processor is configured to determine whether an area of the glass is at a temperature higher than a temperature of said another area of the glass by at least a predetermined amount, and when the area of the glass is at a temperature higher than a temperature of said another area of the glass by at least the predetermined amount determine that the area of the glass may have an inclusion.

29. The system of claim 25, wherein said at least one light source comprises a flash lamp and/or a laser.

30. A system for detecting inclusions in glass including a base glass composition comprising:

| Ingredient | wt. % |
|---|---|
| $SiO_2$ | 67-75% |
| $Na_2O$ | 10-20% |
| CaO | 5-15% |
| $Al_2O_3$ | 0-7% |
| $K_2O$ | 0-7% | the system comprising:

at least one thermal sensor configured to sense temperatures of the glass; and a processor, including processing circuitry, configured to receive temperature data from the at least one thermal sensor and detect an inclusion in the glass based at least on a temperature difference between the inclusion and another area of the glass.

* * * * *